(12) United States Patent
Patno et al.

(10) Patent No.: US 7,396,677 B2
(45) Date of Patent: Jul. 8, 2008

(54) METHOD OF PREPARING NUCLEIC ACIDS FOR DETECTION

(75) Inventors: Tim Patno, Chicago, IL (US); Jennifer Hollenstein, Grayslake, IL (US); Christian Kronshage, Round Lake, IL (US); Christopher Khoury, Chicago, IL (US); Mark Weber, Algonquin, IL (US); Tom Westberg, Gurnee, IL (US); William Cork, Lake Bluff, IL (US)

(73) Assignee: Nanosphere, Inc., Northbrook, IL (US)

( * ) Notice: Subject to any disclaimer, the term of this patent is extended or adjusted under 35 U.S.C. 154(b) by 296 days.

(21) Appl. No.: 10/703,368

(22) Filed: Nov. 7, 2003

(65) Prior Publication Data

US 2005/0112583 A1     May 26, 2005

(51) Int. Cl.
    *C12M 1/34*       (2006.01)
    *C12M 3/00*       (2006.01)
    *C12M 1/22*       (2006.01)
    *B01L 3/00*       (2006.01)
    *B01L 3/02*       (2006.01)

(52) U.S. Cl. .............. 435/288.5; 435/288.2; 435/288.3; 435/288.4; 435/305.1; 435/305.2; 435/305.3; 435/287.2; 422/99; 422/100

(58) Field of Classification Search .............. 435/288.5, 435/288.4, 288.3, 288.2, 305.1, 305.2, 305.3; 422/99, 100
See application file for complete search history.

(56) References Cited

U.S. PATENT DOCUMENTS

| | | | |
|---|---|---|---|
| 5,587,128 A | | 12/1996 | Wilding et al. |
| 6,340,598 B1 | * | 1/2002 | Herron et al. ............... 436/518 |
| 6,403,379 B1 | * | 6/2002 | Munson et al. ............... 436/43 |
| 6,444,461 B1 | * | 9/2002 | Knapp et al. ............. 435/283.1 |
| 2001/0046702 A1 | * | 11/2001 | Schembri ................. 435/287.2 |
| 2004/0053268 A1 | * | 3/2004 | Karlsen .......................... 435/6 |
| 2004/0087033 A1 | * | 5/2004 | Schembri .................... 436/180 |
| 2004/0229247 A1 | * | 11/2004 | DeBoer et al. ................. 435/6 |
| 2004/0248318 A1 | * | 12/2004 | Weinberger et al. ......... 436/173 |
| 2005/0214854 A1 | * | 9/2005 | Dahm et al. ................... 435/6 |
| 2005/0271551 A1 | * | 12/2005 | Shumate et al. ............ 422/100 |
| 2006/0051798 A1 | * | 3/2006 | Mirkin et al. .................. 435/6 |
| 2007/0098600 A1 | * | 5/2007 | Kayyem .................... 422/102 |

\* cited by examiner

*Primary Examiner*—William H. Beisner
*Assistant Examiner*—Nathan Bowers
(74) *Attorney, Agent, or Firm*—Gregory T. Pletta

(57) ABSTRACT

A method and apparatus are provided for preparing a test sample for detecting a predetermined target nucleic acid. The method includes the steps of providing a test probe comprising an oligonucleotide attached to a nanoparticle and providing a hybridization unit containing the test sample and the test probe, wherein said hybridization unit further includes a target sample substrate and a distribution manifold coupled to a first side of the substrate. The method further includes the steps of clamping a processing fluids manifold to the distribution manifold of the hybridization unit, denaturing the test sample and preparing the test sample for detecting the predetermined target nucleic acid by pumping a plurality of processing fluids between the processing fluids source manifold and distribution manifold to hybridize the test probe and predetermined target nucleic acid to the target sample substrate, to wash the hybridized sample and to amplify a detectable parameter of the hybridized sample.

14 Claims, 13 Drawing Sheets

USER INSTALLS REAGENTS AND WASTE CONTAINERS

USER PREPARES HYBRIDDIZATION UNIT

INSIDE THE DEVICE - HYBRIDIZATION

INSIDE THE DEVICE - WASH

INSIDE THE DEVICE - AMPLIFICATION

1. SILVER A AND SILVER B ARE ADDED TO ENHANCE THE SIGNAL

2. AFTER AMPLIFICATION, THE SILVER SOLUTION IS PURGED TO WASTE CONTAINER.

INSIDE THE DEVICE - STOP

1. STOP SOLUTION IS ADDED TO STOP AMPLIFICATION

2. AFTER THE STOP, THE STEP IS COMPLETED. THE STOP SOLUTION IS PURGED TO WASTE CONTAINER.

INSIDE THE DEVICE - FLUSH

SLIDE REMOVAL AND IMAGING

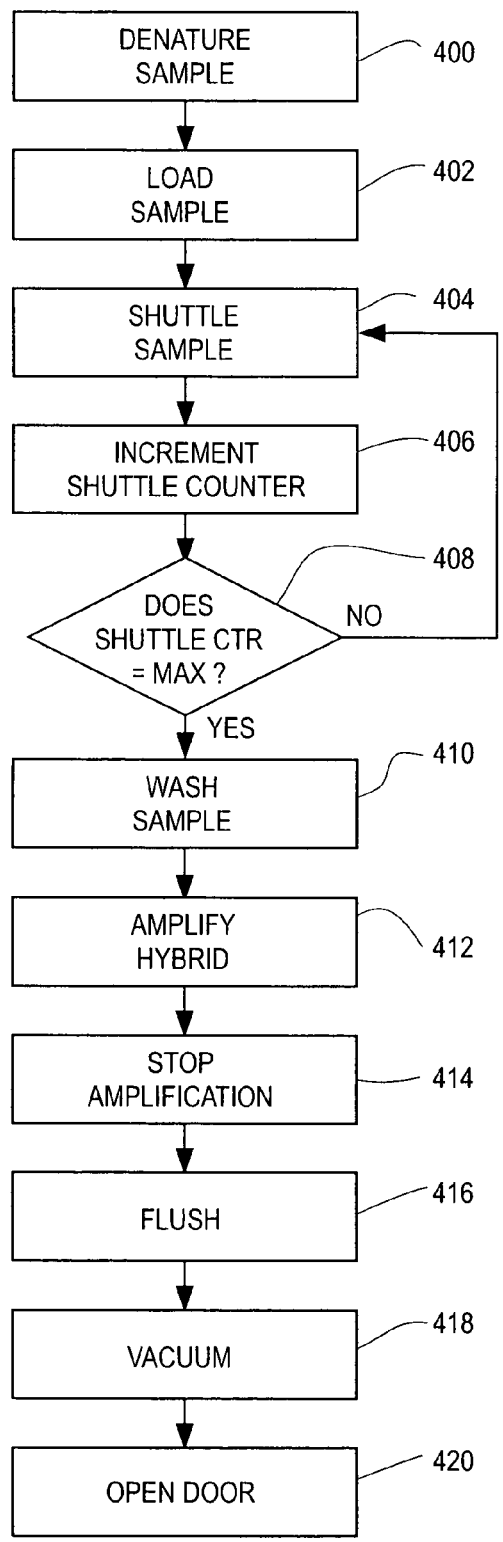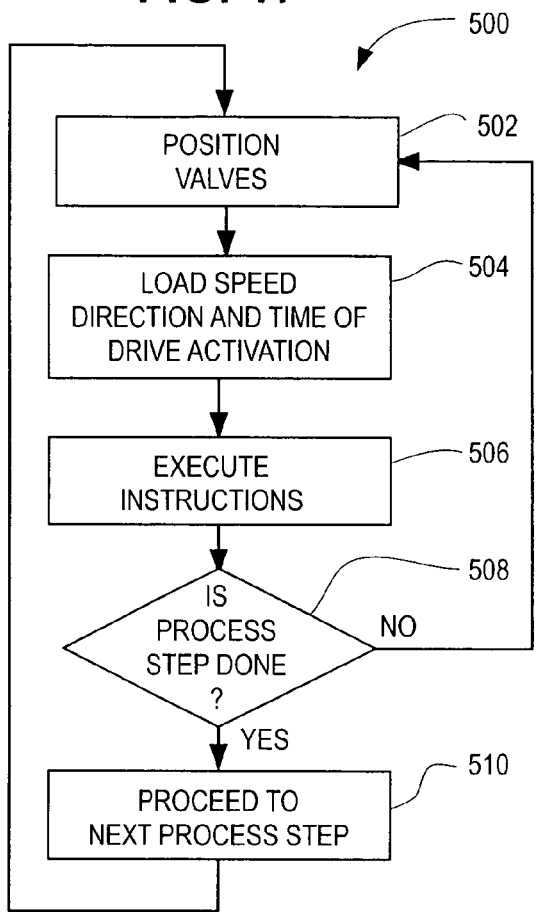
FIG. 16
FIG. 17

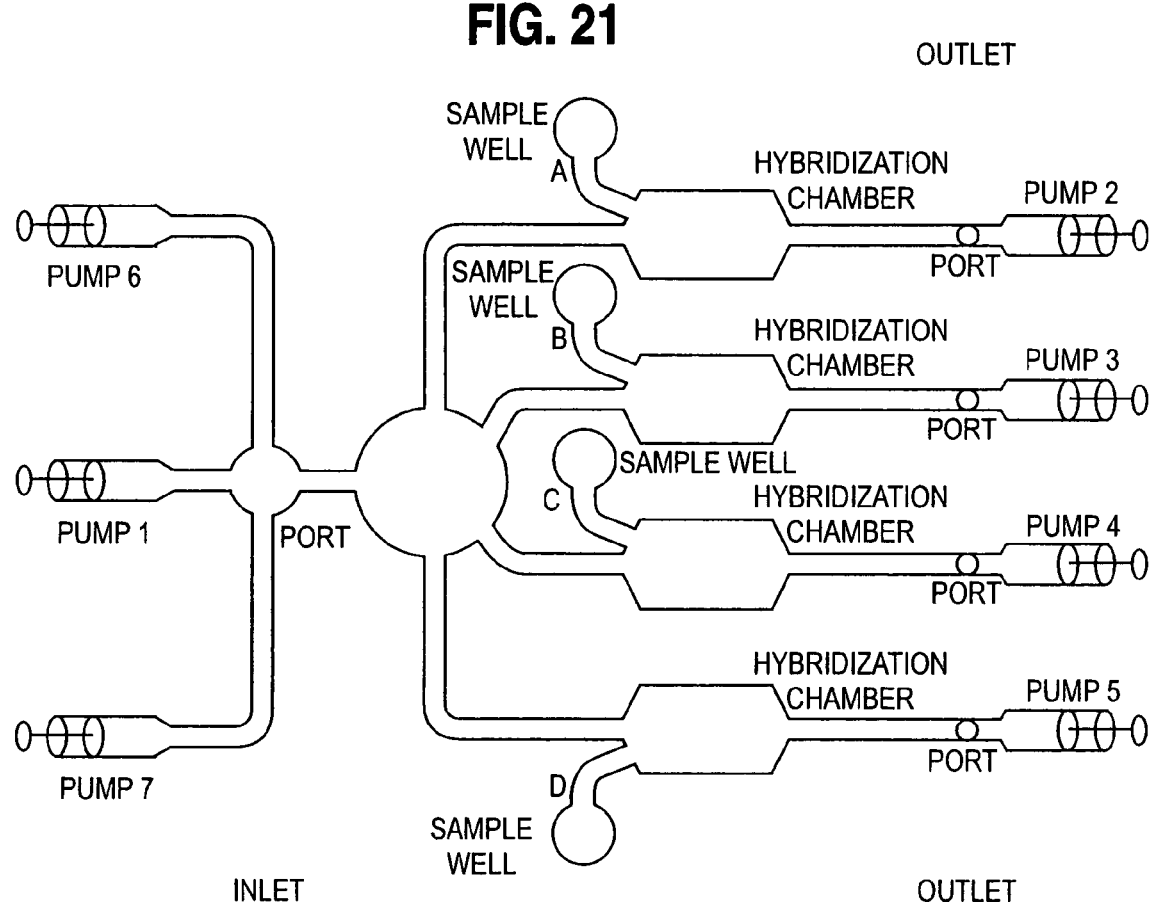

METHOD OF PREPARING NUCLEIC ACIDS FOR DETECTION

FIELD OF THE INVENTION

The field of the invention relates to biological testing and more particularly to detecting nucleic acids.

BACKGROUND OF THE INVENTION

Methods of detecting nucleic acids are generally known. In fact, there are a number of methods available for detecting specific nucleic acid sequences.

Known methods include those based upon electrophoresis, polymerase chain reaction (PCR) processes, various hybridization techniques, and a number of other techniques. While these methods are effective, they are all time consuming, costly and subject to significant human error.

For example, one manufacturer makes a microfluidics system that hybridizes a sample to a chip followed by staining of the chip. The hybridization process takes approximately 12 hours. Staining takes approximately 1.5 hours to complete.

Another supplier provides a system that relies upon a single nucleotide polymorphism (SNP) technique. This system uses a microchip for performing multiple assays. Probes are added to a cartridge and the particles move based on charge in an electric field. A detection system may be used for analyzing the cartridges after hybridization with the sample DNA.

Still another supplier provides a device called a Lightcycler that combines PCR amplification and DNA detection into one process. The Lightcycler can use one of two processes for detection. The first process relies upon PCR and hybridization. The second process relies upon PCR and dye and melting curve analysis.

The development of reliable methods for detecting and sequencing nucleic acids is critical to the diagnosis of genetic, bacterial and viral diseases. Because of the importance of health care and disease prevention, a need exists for quicker and cheaper methods of identifying nucleic acids.

SUMMARY

A method and apparatus are provided for preparing a test sample for detecting a predetermined target nucleic acid. The method includes the steps of providing a test probe comprising an oligonucleotide attached to a nanoparticle and providing a hybridization unit containing the test sample and the test probe, wherein said hybridization unit further includes a target sample substrate and a distribution manifold coupled to a first side of the substrate. The method further includes the steps of clamping a processing fluids manifold to the distribution manifold of the hybridization unit, denaturing the test sample and preparing the test sample for detecting the predetermined target nucleic acid by pumping a plurality of processing fluids between the processing fluids source manifold and distribution manifold to hybridize the test probe and predetermined target nucleic acid to the target sample substrate, to wash the hybridized sample and to amplify a detectable parameter of the hybridized sample.

BRIEF DESCRIPTION OF THE DRAWINGS

FIG. 16 is a flow chart of method steps that may be followed by the sample processing system of FIG. 1;

FIG. 17 is a flow chart of a process control application;

FIG. 21 depicts a fluid flow schematic for sample processing under an alternate embodiment of the invention.

DETAILED DESCRIPTION OF AN ILLUSTRATED EMBODIMENT

Figure 1:
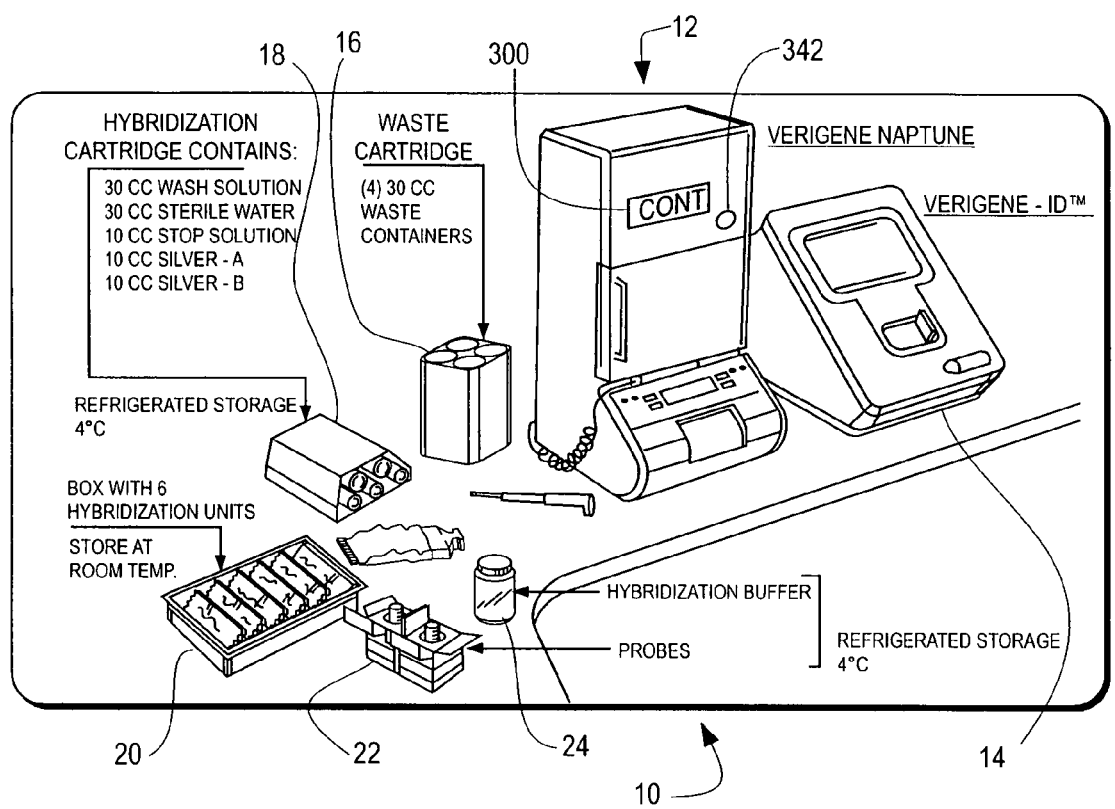
FIG. 1 depicts a nucleic acid testing system in accordance with an illustrated embodiment of the invention.

FIG. 1 is a perspective view of a nucleic acid detection system 10, shown generally in accordance with an illustrated embodiment of the invention. The processing system 10 may be used for the detection of any of a number of predetermined target nucleic acids. In fact, any type of nucleic acid may be detected, and the methods may be used for the diagnosis of disease and in sequencing of nucleic acids. Examples of nucleic acids that can be detected by the methods of the invention include genes (e.g., a gene associated with a particular disease), viral RNA and DNA, bacterial DNA, fungal DNA, cDNA, mRNA, RNA and DNA fragments, oligonucleotides, synthetic oligonucleotides, modified oligonucleotides, single-stranded and double-stranded nucleic acids, natural and synthetic nucleic acids, etc. Examples of the uses of the methods of detecting nucleic acids include: the diagnosis and/or monitoring of viral diseases (e.g., human immunodeficiency virus, hepatitis viruses, herpes viruses, cytomegalovirus, and Epstein-Barr virus), bacterial diseases (e.g., tuberculosis, Lyme disease, *H. pylori*, *Escherichia coli* infections, *Legionella* infections *Mycoplasma* infections, *Sammonella* infections), sexually transmitted diseases (e.g., gonorrhea), inherited disorders (e.g., cystic fibrosis, Duchene muscular dystrophy, phenylketonuria, sickle cell anemia), and cancers (e.g., genes associated with the development of cancer); in forensics; in DNA sequencing; for paternity testing; for cell line authentication; for monitoring gene therapy; and for many other purposes.

Included within the system 10 may be a sample processing system 12 and a optical reader 14 for reading samples automatically prepared by the sample processing system 12. The optical reader 14 may be a model Verigene IDT™ made be Nanophere, Inc. of Northbrook, Ill.

The sample processing system 12 may include a controller 300 and a number of functionally distinct elements used for storage and handling of processing solutions and samples. For example, the processing system 12 may include one or more removable hybridization units 20. The hybridization unit 20 may be used by the processing system 12 as a processing vessel for detecting the predetermined target nucleic acid(s).

The detection system 10 may also require a number of processing solutions for preparing the nucleic acids for detection. For example, the processing system 12 may require one or more probes 22 and a hybridization buffer fluid (solution) 24. In addition, a processing fluids package 18 may be provided that includes a wash solution, sterile water, one or more amplifying solutions (e.g., silver part A, silver part B, etc.) and a stop solution.

The hybridization unit 20 (FIG. 2) may include at least three functionally separate portions. A target sample substrate 42 of optically transparent glass may be provided as a base for processing the predetermined nucleic acid. A distribution manifold 44 may be provided that contacts the substrate and that, together with the substrate 42 and a silicone gasket 58, define the chambers and passageways that allow flow of processing solutions through the hybridization unit 20. Finally, a base 40 is provided that supports the substrate 42.

The manifold 44 may be provided with a flange 43, 45 on opposing sides that each contain a set of apertures 56 that resiliently engages a complementary set of pegs 54 on the base. The pegs 54 may be provided with a taper on the engagement side to allow the flange to resiliently expand over and allow the apertures 56 to engage the pegs 54. The silicone gasket 58 (provided on the engagement side of the manifold 44) allows the manifold to resiliently engage with the substrate 42 and define a seal around a periphery of chambers and passageways of the hybridization unit 20.

Figure 3:
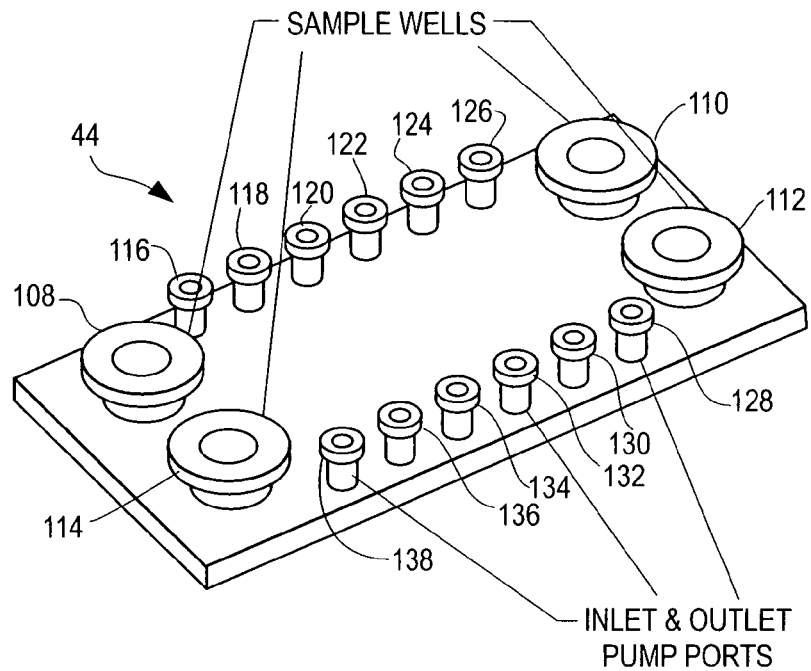
FIG. 3 depicts a manifold that may be used with the hybridization unit of FIG. 2.
Figure 4:
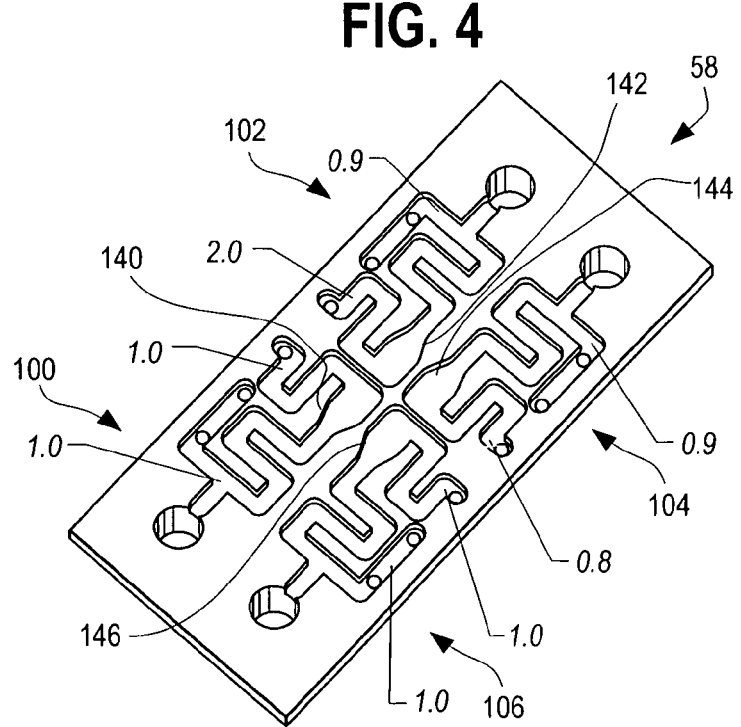
FIG. 4 depicts a gasket that may be used with the hybridization unit of FIG. 2.

FIG. 3 depicts a simplified view of the manifold 44. FIG. 4 depicts the silicone gasket 58.

As shown in FIGS. 3 and 4, each hybridization unit 20 may include four sample processing areas 100, 102, 104, 106. Each processing area 100, 102, 104, 106 may include a hybridization zone 140, 142, 144, 146, an associated sample well 108, 110, 112, 114, three processing ports 116, 118, 120; 122, 124, 126; 128, 130, 132; 134, 136, 138 associated with each respective hybridization zone 140, 142, 144, 146 and interconnecting passageways (shown disposed in the gasket in FIG. 4).

FIG. 4 shows a range of gasket depths that may be used in conjunction with sample processing. It may be noted that the varying depths may be used to minimize flow resistance in the channels while maximizing fluid mixing and interaction among the hybridizing elements within the hybridization chamber 140, 142, 144, 146.

In preparation for testing for a particular nucleic acid, a first oligonucleotide or first group of oligonucleotides 46, 48, 50, 52 with a first predetermined genetic sequence may be disposed on the substrate 42 (FIG. 2) within each of the hybridization zones 140, 142, 144, 146. The first oligonucleotides 46, 48, 50, 52 may have a genetic sequence that is complementary to a first portion of the genetic sequence of the predetermined target nucleic acid.

The probes 22 may be constructed of nanoparticles with one or more strands of second oligonucleotides of a second predetermined genetic sequence attached to the nanoparticles. Nanoparticles useful in the practice of the invention may include metal (e.g., gold, silver, copper, and platinum), semiconductor (e.g., CdSe, CdS, and CdS or CdSe coated with ZnS) and magnetic (e.g., ferromagnetite) colloidal materials. Other nanoparticles useful in the practice of the invention include ZnS, ZnO, $TiO_2$, AgI, AgBr, $HgI_2$, PbS, PbSe, ZnTe, CdTe, $In_2S_3$, $Cd_3P_2$, $Cd_3As_2$, InAs, and GaAs. The size of the nanoparticles is preferably from about 5 nm to about 150 nm (mean diameter), more preferably from about 5 to about 50 nm, most preferably from about 10 to about 30 nm.

The nanoparticles, the second oligonucleotides or both are functionalized in order to attach the oligonucleotides to the nanoparticles. Such methods are known in the art. For instance, oligonucleotides functionalized with alkanethiols at their 3'-termini or 5'-termini readily attach to gold nanoparticles.

The second oligonucleotides may have a sequence that is complementary to a second portion of the genetic sequence of the predetermined target nucleic acid. Preparation of the first and second oligonucleotides and attachment to the respective particles and substrate may be accomplished generally as described in U.S. Pat. No. 6,417,340 assigned to the assignee of the present invention and incorporated herein by reference.

In general, the test probe and test sample (that may or may not contain the predetermined target nucleic acid) and a hybridization fluid may be mixed in a sample well. The mixture may be denatured and passed through the hybridization chamber. Denaturing may be accomplished using any known process (e.g., heat, chemical, etc.).

Within the hybridization chamber, the test probe and predetermined nucleic acid may hybridize with the first oligonucleotide. The optical characteristics of the hybridized materials may be enhanced (e.g., plating a silver solution to the nanoparticles of the hybrid). After enhancement, any hybridized materials may be detected optically within the optical reader 14. In this case, the plating of the silver solution to the gold nanoparticles of the hybrid amplifies the optical reflectivity of the hybrid. The optical reflectivity may then be compared with a threshold value to confirm the presence of the target nucleic acid.

Alternatively, the detectable parameter may be resistance. In this case, the silver plated to the gold nanoparticle within the hybrid amplifies a current path through the hybrid. The resistance may then be compared with a threshold value to confirm the presence of the target nucleic acid.

Turning now to operation of the sample processing system 14, an explanation will now be provided of the controller 300 and the interaction of the controller 300 with the hybridization unit 20. In this regard, FIG. 5 depicts the controller 300 and various actuating elements used by the sample processing system 12 in processing samples within the hybridization unit 20.

Figure 5:
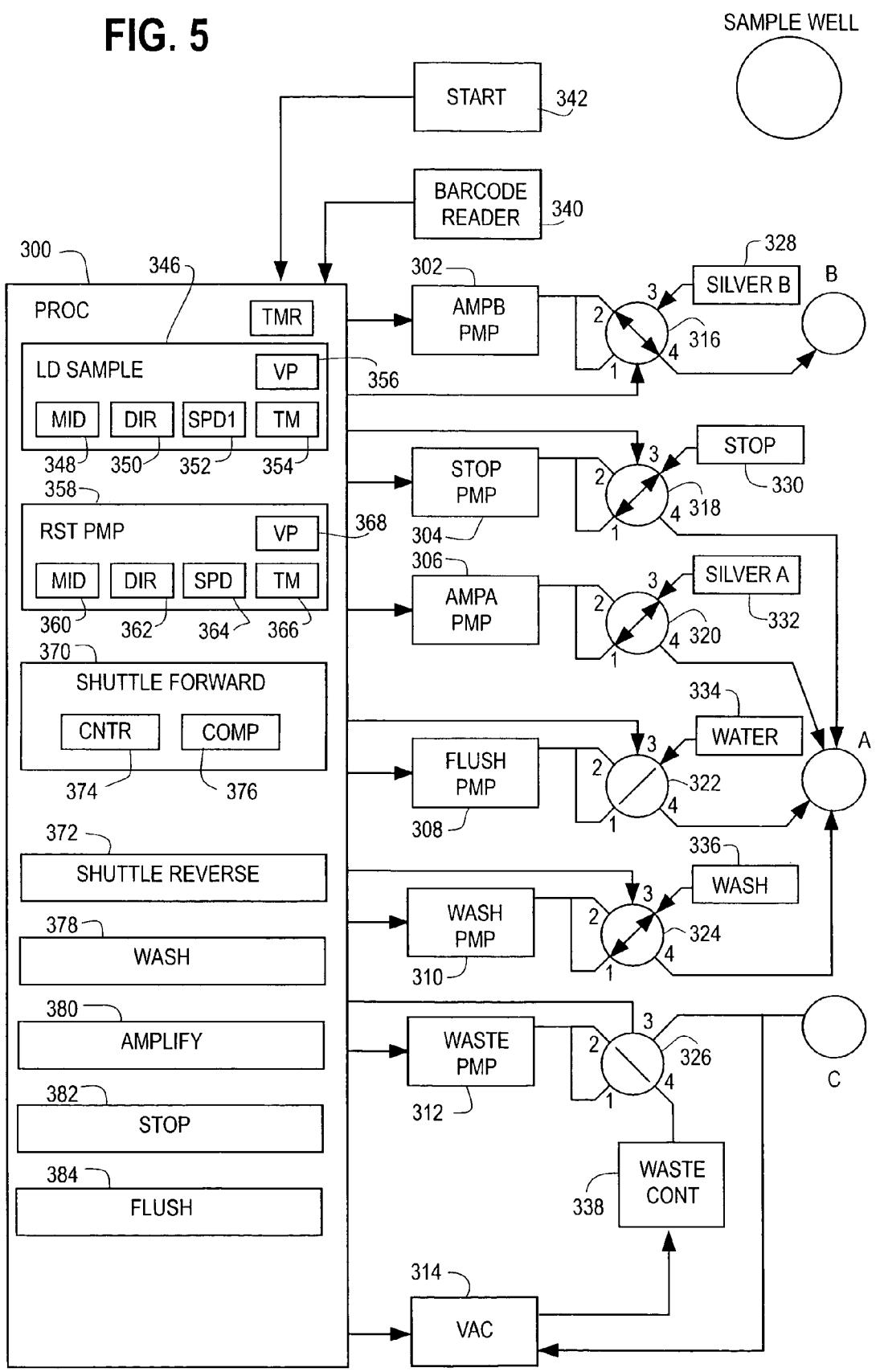
FIG. 5 is a schematic of controls that may be used to control the sample processing unit of FIG. 1.

Along the right side of FIG. 5 is shown a set of ports labeled "SAMPLE WELL, B, A, C". The reference "SAMPLE WELL" may be used to refer to large ports 108, 110, 112, 114 in FIG. 3. Similarly, port B may be used to refer to smaller ports 116, 126, 128, 138, port A may be used to refer to ports 118, 124, 130, 136 and port C may be used to refer to ports 120, 122, 132, 134.

Processing of samples in sample processing areas 100, 102, 104, 106 may be assumed to be substantially identical. It should be noted in this regard that while the processing may be substantially identical for each sample processing area 100, 102, 104, 106, the target nucleic acid that is detected may be different within each of the four areas 100, 102, 104, 106.

As shown in FIG. 5, the sample processing system 12 may include a number of pumps 302, 304, 306, 308, 310, 312 and a vacuum source 314. While any form of pump 302, 304, 306, 308, 310, 312 may be used, it is contemplated that a positive displacement pump such as a syringe pump may be used for reasons that will become apparent from the description below.

The syringe pumps may include a syringe body and a linear actuator. The linear actuator may be programmed by the controller 300 to fill and empty at precisely controlled rates.

The routing of fluids to and from the pumps 302, 304, 306, 308, 310, 312 may be controlled by a number of multiport valves 316, 318, 320, 322, 324, 326. While any number of ports may be used, it is believed that the four-port valves 316, 318, 320, 322, 324, 326 shown in FIG. 5 are particularly well adapted to the purpose described below.

In this regard, the valves 316, 318, 320, 322, 324, 326 may have ports labeled 1-4. A spool within the valves 316, 318, 320, 322, 324, 326 may allow any two opposing ports to be connected together (e.g., port 1 may be connected to port 3 or port 2 may be connected to port 4).

When used with syringe pumps 302, 304, 306, 308, 310, 312, muliport valves 316, 318, 320, 322, 324, 326 allow a precise amount of a selected fluid to be transferred at each stage of processing. For example, with ports 1 and 3 of valve 322 connected (as shown in FIG. 5), the syringe pump 308 may withdraw a precise amount of water from the water container 334 on a fill portion of the pump cycle. The multiport valve 322 may then be actuated to connect ports 2 and 4. The water previously drawn into the syringe pump 308 may now be discharged through port 4 of valve 322 and into port A of the hybridization unit 20.

It may be noted that in some applications, the valves 316, 318, 320, 322, 324, 326 and containers 328, 330, 332, 334, 336, 338 may not be needed. For example, the valves and containers would not be needed in cases where the total flow for each function is less than the capacity of the syringe pump 302, 304, 306, 308, 310. In these cases, the syringe pump may simply be replaced after each testing procedure or after multiples of each testing procedure.

FIG. 21 illustrates fluid flow for sample processing under an even more preferred embodiment of the invention. In the example of FIG. 21, fluidic control is maintained without the use of valves by utilizing pumps on the inlet and outlet ports to route fluids down a specified path.

By introducing fluids via pump 1 and only withdrawing fluids via pump 2, the fluid can be routed through hybridization chamber and flow path A. Fluids can also be routed down multiple paths in parallel by actuating the control pumps (2, 3, 4 or 5) for that fluid path. Parallel fluid processing may be useful to reduce processing time when high tolerance pumping is not required, such as during washing and rinsing steps.

Other additional pumps on the inlet side (not shown in FIG. 21) will provide additional fluids. A system such as that shown in FIG. 21 with 8 inlet pumps for 8 specific fluids can perform a variety of nucleic acid tests. The type of tests can be selected by the insertion of various fluids into the flow paths from the 8 pump chambers.

Access to fluids inserted into the sample well by the user is accomplished by pulling on the outlet pump(s) only. The sample well is designed to easily collapse and block flow so that the target sample will flow preferentially only out of the specific sample well for the specific flow path and outlet pump desired.

Figure 6:
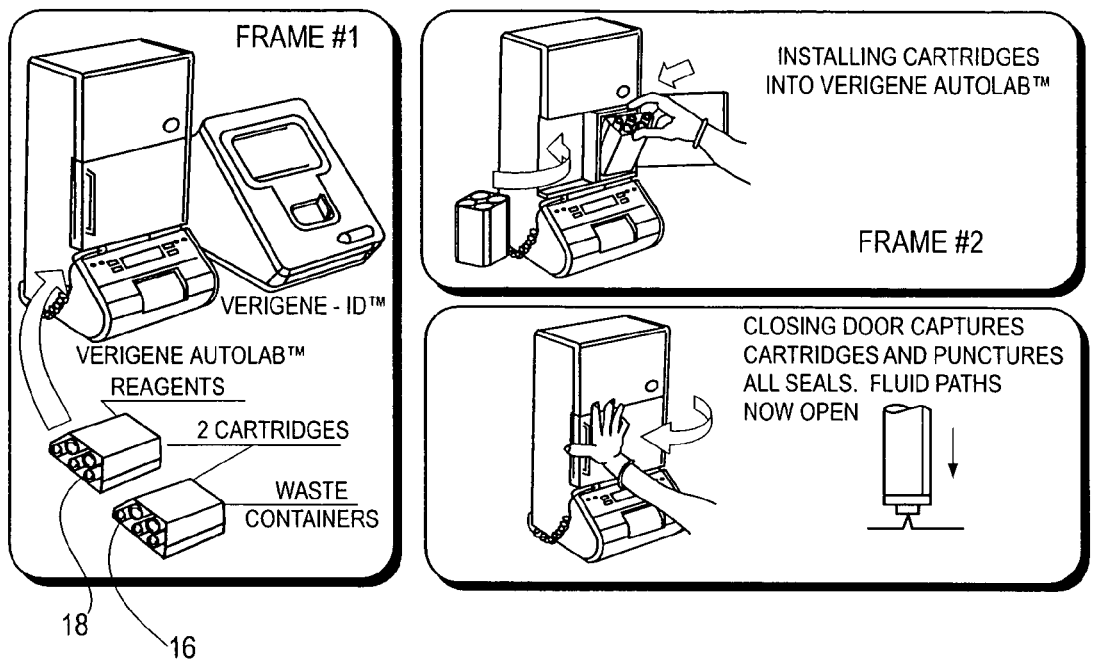
FIG. 6 depicts preparatory steps that may be used in conjunction with the sample processing system of FIG. 1.

FIGS. 6-16 show process steps that may be used in detecting the predetermined nucleic acid. For example, Frame #1 of FIG. 6 shows the preliminary step of providing a reagent cartridge 18 and a waste container 16. Frame #2 shows the loading of the cartridges 16, 18 into the sample processing system 12. Frame #3 shows the closing of the door and references the fact that closing the door causes a set of connection fittings to puncture the seals on the reagent and waste containers. Alternatively, or in addition, closing the door provides a signal to the controller which then controls linear actuators to engage the pumps which provides fluid(s) for processing. A bar code reader 340 may be provided to read a bar code on the reagent cartridge to automatically verify that the correct reagent cartridge has been inserted.

Figure 7:
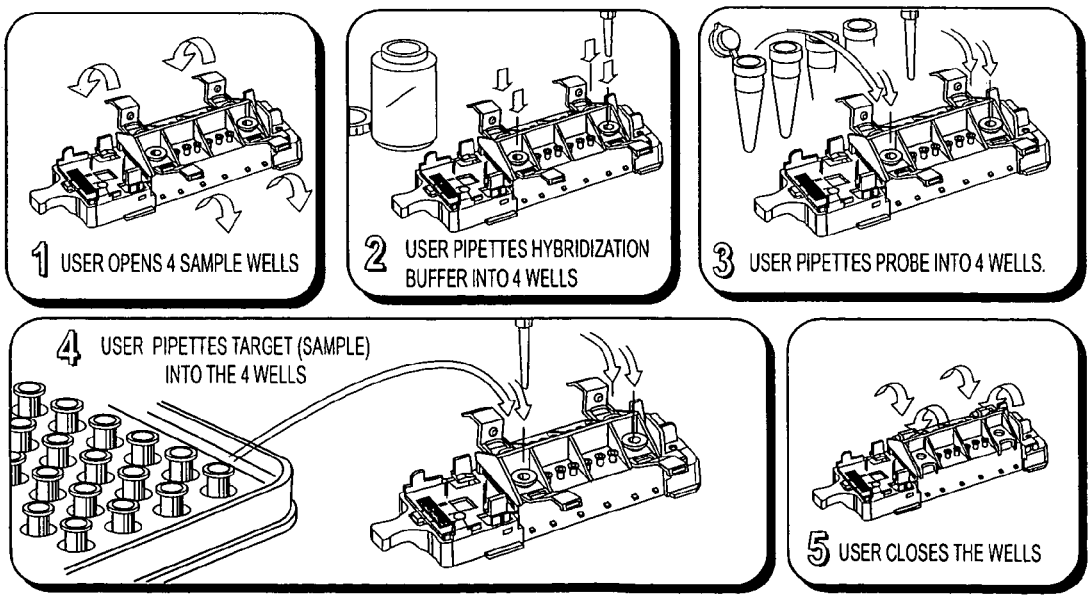
FIG. 7 depicts preparatory steps that may be used in conjunction with the hybridization unit of FIG. 2.

FIG. 7 shows preparation of the hybridization unit 20. Frame #1 shows a user opening a set of lids covering the four sample wells 108, 110, 112, 114. The user than pipettes a hybridization buffer into the four wells 108, 110, 112, 114 as shown in Frame #2. The user then pipettes the probe 24 into the four wells 108, 110, 112, 114, as shown in Frame #3. As a fourth step, the user pipettes a sample that may contain the predetermined target nucleic acid into the well 108, 110, 112, 114 as shown in Frame #4. Finally, the user closes the lids on the wells 108, 110, 112, 114 as shown in Frame #5. Alternatively, the user may provide only the predetermined target nucleic acid into the sample well or a combination of the predetermined target nucleic acid and hybridization buffer or predetermined target nucleic acid and probe into the sample well.

Figure 8:
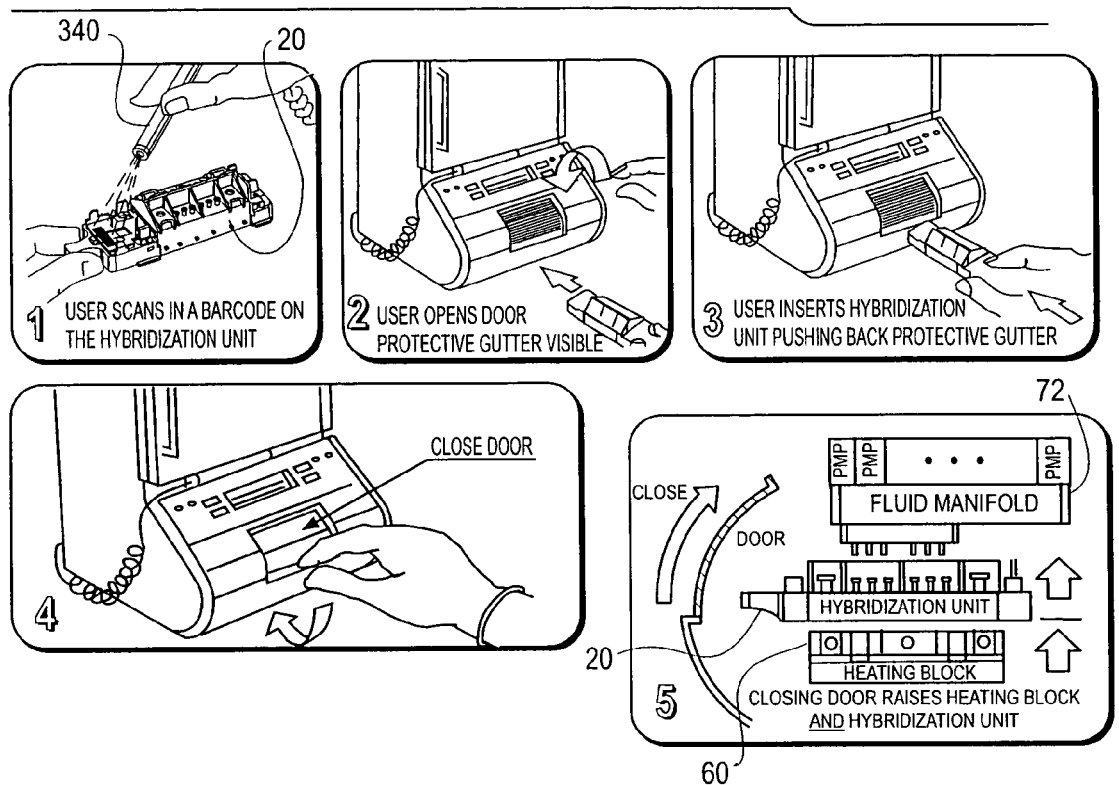
FIG. 8 depicts loading steps that may occur when the hybridization unit of FIG. 2 is loaded into the sample processing system of FIG. 1.

FIG. 8 shows preparation and loading of the hybridization unit 20 into the sample processing system 12. As a first step, shown in Frame #1 of FIG. 8, the user may use a barcode reader 340 to identify the hybridization unit 20 to the system 12. Alternatively, the bard code reader may be embedded inside the loading door of the system and the bar code may be read when the hybridization unit is loaded into the system.

To load the hybridization unit 20, the user may open a door on the sample processing system 12. A spring-loaded receptacle that catches fluid from a fluid manifold 72 of the processing system 12 is found extended to a fully forward position as shown in Frame 2 of FIG. 8. The user then pushes the hybridization unit 20 into the sample processing system 12 as shown in Frame #3 and closes the door (Frame #4).

Activation of the sample processing system 12 may occur by closure of the door or by activating a START button 342. In either case, activation of the system 12 causes the hybridization unit 20 to be raised into contact with a processing fluids manifold 72 and a heating/cooling block 60 to be raised into contact with the hybridization unit 20. The raising of the hybridization unit 20 and heating/cooling block 60 may be accomplished by a simple mechanical linkage connected to the door or through a linear actuator coupled to an elevator assembly.

The raising of the hybridization unit 20 creates a fluid-transfer connection between the ports 116, 118, 120, 122, 124, 126, 128, 130, 132, 134, 136, 138 of the hybridization unit 20 and respective ports of the processing fluids manifold 72 and with the pumps 1-7 of FIG. 21 or with respective valves 316, 318, 320, 322, 324, 326 and with pumps 302, 304, 306, 308, 310, 312, 314 of the sample processing system 12 of FIG. 5. Similarly, the raising of the heating/cooling block 60 causes a thermal transfer connection between the hybridization unit 20 and the heating/cooling block 60.

Figure 9:
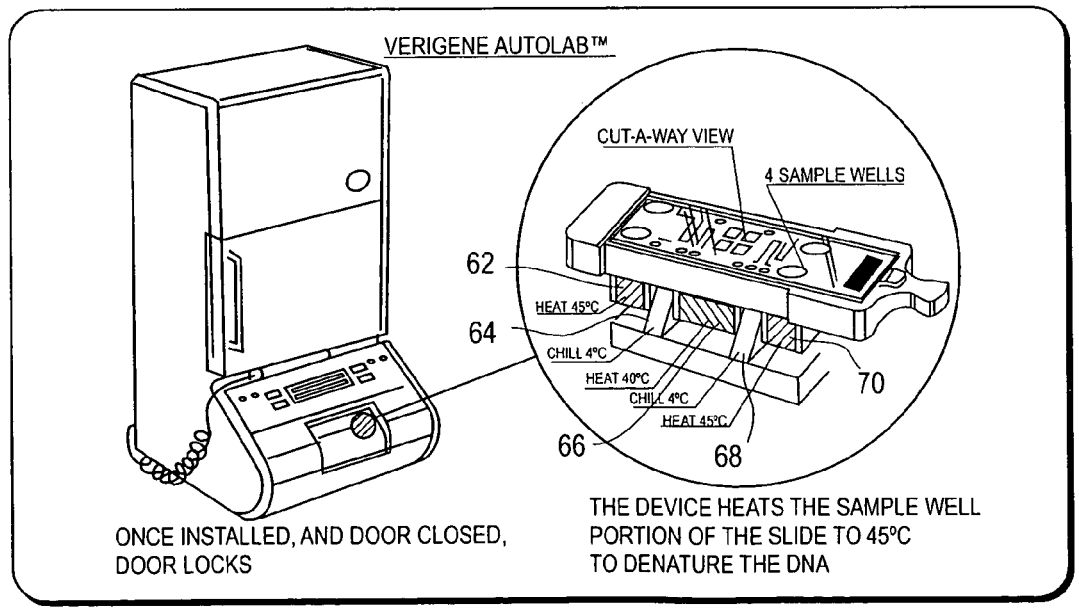
FIG. 9 depicts operation of the heating/cooling unit of FIG. 8.

FIG. 9 depicts a preliminary processing step 400 (FIG. 16) performed by the sample processing system 12. As shown, a first heating element 62 and a second heating element 70 of the heating/cooling block 60 connect to and heat the sample wells 108, 110, 112, 114 to a temperature for denaturing the samples (e.g., 95° C.) of the predetermined target nucleic acid. As used herein, denature means to cause the tertiary structure of the nucleic acid to unfold.

A first cooling element 64 and a second cooling element 68 function to cool the denatured samples as they are transferred from the sample wells 108, 110, 112, 114 to hybridization chambers 140, 142, 144, 146. A third heating element 66 is located adjacent the hybridization chambers 140, 142, 144, 146 to heat the samples to a specified temperature for hybridization (e.g., 40° C.).

Figure 10:
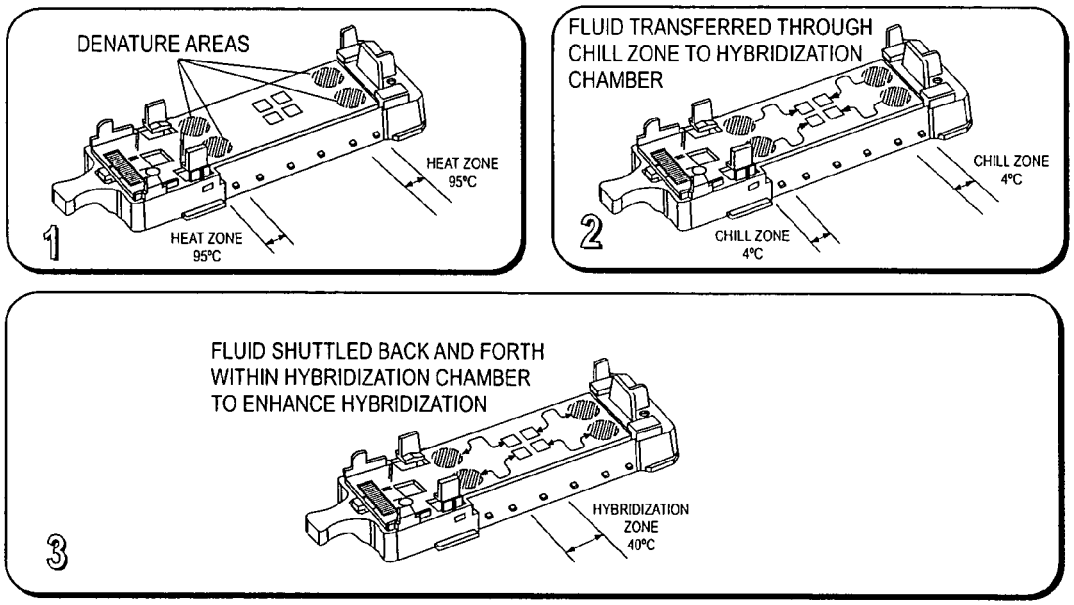
FIG. 10 depicts fluid flows in the hybridization unit of FIG. 2.

Frame #1 of FIG. 10 depicts the heating of the samples in the sample wells 108, 110, 112, 114 to the denaturing temperature (e.g., 95° C.). Frame #2 of FIG. 10 depicts loading 402 of the samples by transferring the samples through the chill zone into the hybridization chambers 140, 142, 144, 146. Transfer of the samples from the sample wells 108, 110, 112, 114 may be accomplished by activating the waste pump 312 with the waste valve 324 in the position shown in FIG. 5. The transfer of the samples across the chill zone may be accomplished by the controller 300 choosing a relatively slow rate of fluid transfer (e.g., 1 cc/min) as the pump 312 pulls fluid from port C to ensure proper cooling of the samples as they pass over the chill zone.

It may be noted that to load the sample into the hybridization zone 140, 142, 144, 146, the controller 300 may retrieve and execute a set of valve and motor control parameters (instructions) 346 from memory for controlling a linear actuator of the pump 312. The parameters 346 may include a motor identifier 348, a direction 350, a speed 352, a time 354 and a valve position 356.

If the linear actuator has its own controller, then the direction 350, speed 352 and time may be simply downloaded to the controller for execution. If the controller is provided through the use of special purpose programs within the controller 300, then execution of the instructions may be provided from within the controller 300.

It should be noted that (before loading of the samples) the hybridization chambers 140, 142, 144 may initially have been filled with air. As such, the fluid pulled from port C would be air. The withdrawal of air from port C pulls the samples from the sample wells 108, 110, 112, 114 into the hybridization chambers 140, 142, 144, 146.

As a final step in the process of loading the sample, the controller 300 may reset the waste pump 310. Resetting the waste pump 310 may means retrieving a set of instructions 358 from memory. The instructions 358 may contain an instruction 368 that causes the waste valve 326 forms a connection between ports 2 and 4. The instructions 358 may also contain a motor identifier 360, a direction 362, a speed 364 and a time 366 necessary to cause the waste pump 310 to move to a fully discharged position.

It may be noted that the instructions for loading the sample and for resetting the waste pump 310 and for performing the other process steps described herein may be accomplished by a process control application depicted in FIGS. 16 and 17. FIG. 16 may be used to depict the overall functionality of the control application and FIG. 17 may be used to depict the activity performed within the individual blocks of FIG. 16.

With respect to execution of the control application, activation of the START button 342 or closing the door brings the hybridization unit 20 into contact with the manifold 72 and heating/cooling block 60. Activation may also start a timer within the controller 300 to detect completion of the denaturization process 400. From the nenaturization process 400, the control application proceeds to the load sample process 402. As a first step of the load sample process 402, the application 500 loads and executes the load sample file 346. As a second step, the application 500 loads and executes the reset pump files 358. In each case, the application 500 positions the valves, loads actuator positioning parameters and executes the positioning parameters. Once each process is complete, the application 500 advances to the next process step.

Frame #3 of FIG. 10 depicts hybridization of the sample and probe with the oligonucleotide strands within hybridization chamber 140, 142, 144, 146. In this case, the controller 300 functions to shuttle 404 the partially hybridized sample and probe back and forth across the hybridization chamber 140, 142, 144, 146.

To shuttle the partially hybridized sample back and forth across the hybridization chamber 140, 142, 144, 146, the application 500 retrieves and execute a set of instructions 370, 372 that activate the wash pump 310 and waste pump 312 to move in opposite directions. In this case, the instructions 370, 372 would cause the wash valve 324 to form a connection between ports 2 and 4 and the waste valve 326 to form a connection between ports 1 and 3. The shuttle forward instruction 370 may cause the wash pump 310 to move a predefined distance towards an empty position and the waste pump 312 to move a predefined distance towards a filled position. When the wash pump 310 and waste pump 312 reach the predefined distance, the application 500 would execute the shuttle reverse instructions 372. The shuttle reverse instruction 372 may cause the wash pump 310 to move a similar distance towards a full position and the waste pump 312 to move a similar towards an empty position. When the predetermined distances are reached, the application 500 may again execute the shuttle forward instructions 370.

Each time the application 500 executes the shuttle forward instructions 370, a counter 374 is incremented 406. After each increment, the value within the counter 374 may be compared 408 within a comparator 376 with a shuttle cycle limit value that terminates the shuttling process after a predefined number of cycles.

Since the pumps 310, 312 would initially contain air, the reciprocal action of the pumps 310, 312 would simply push the sample into and out of the passageways on either end of the hybridization chamber 140, 142, 144, 146 with very little if any of the partially hybridized sample entering either pump 310, 312. Shuttling of the partially hybridized sample across the hybridization zones 140, 142, 144, 146 may continue for a time period determined by the identity and type of the sample (e.g., 10-60 minutes).

Figure 11:
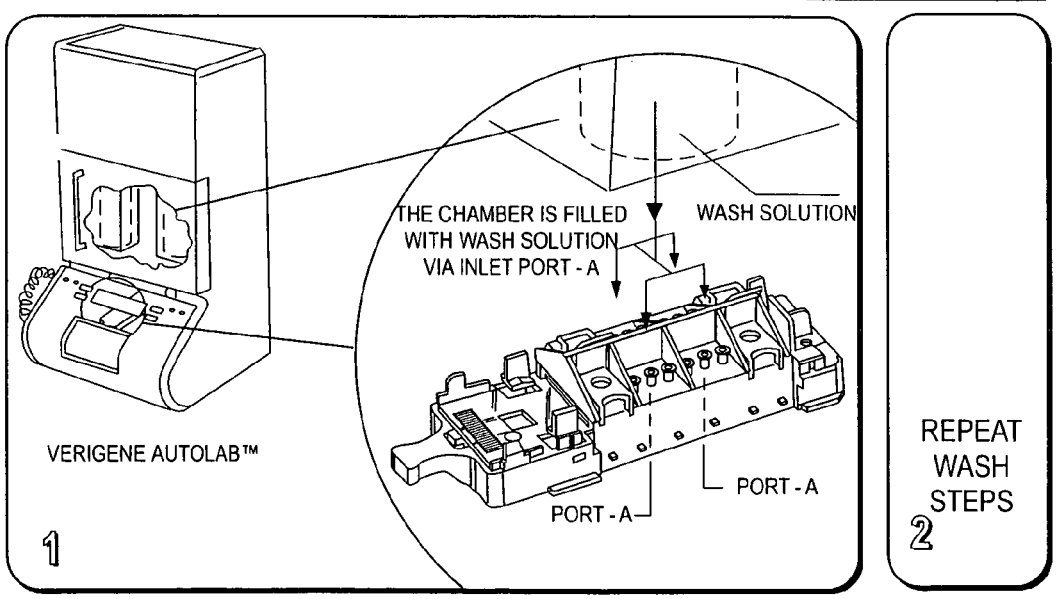
FIG. 11 depicts a wash cycle that may be used with the sample processing system of FIG. 1.
Figure 12:
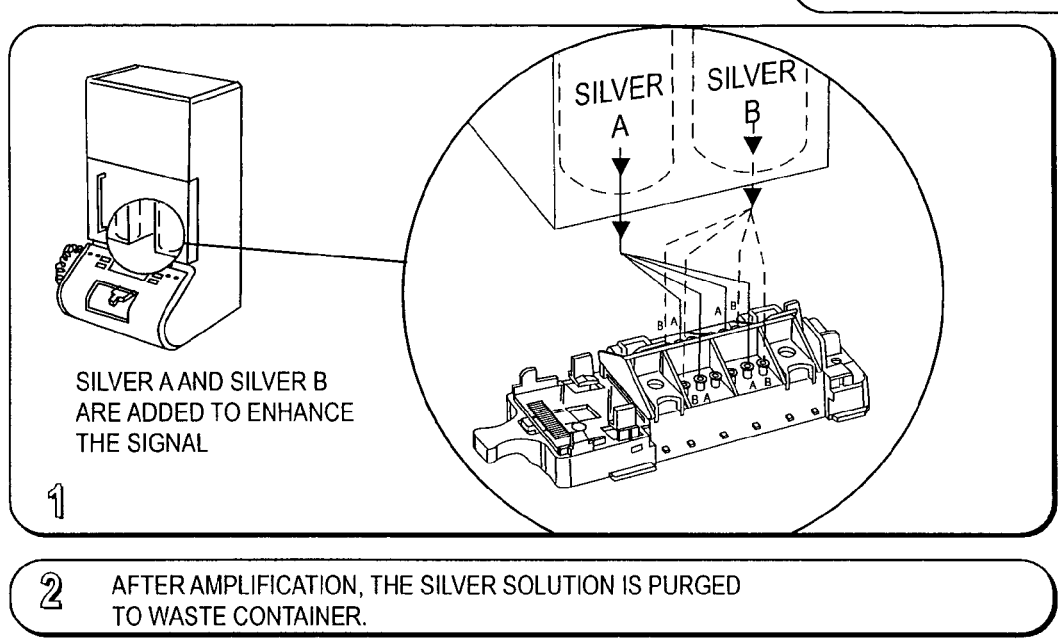
FIG. 12 depicts an amplification step that may be used with the sample processing system of FIG. 1.

Following hybridization of the sample and probe with the oligonucleotide strands within the hybridization chamber 140, 142, 144, 146, the hybridized materials may be washed 410 as shown in Frames #1 and #2 of FIG. 11. To wash the hybridized materials, the controller 300 may execute a set of wash instructions 378 that may concurrently activate the wash pump 310 and the waste pump 312. As a first step, the instructions 378 may cause the wash valve 324 to form a connection between ports 1 and 3. The wash pump 310 may then be activated to draw water from a wash container 336.

Once the syringe pump 310 is full, the instructions 378 may cause the valve 324 to form a connection between ports 2 and 4. The waste valve 326 may also be moved to form a connection between ports 1 and 3. The wash pump 310 and waste pump 312 may be simultaneously activated to operate at the same rate. The wash pump 310 functions to push water into port A and the waste pump 312 functions to pull fluids out of port C.

When the syringe of the wash pump 310 reaches its empty position, the waste pump 312 would reach its full position. At this stage, the wash valve 324 may move to form a connection between ports 1 and 3 and the waste valve 326 may move to form a connection between ports 2 and 4. The wash pump 310 and waste pump 312 may again be activated. In this case, the wash pump 310 now refills from the wash container 336 and the waste pump 312 now discharges into the waste container 338. The fill and empty process may repeat for the number of cycles necessary to flush any unhybridized materials from the hybridization unit 20. A counter may be incremented after each fill and empty cycle and a value within the counter may be compared with a cycle limit within a comparator to determine completion of the wash cycle.

Once the hybridized materials have been washed, a detectable parameter of the hybridized materials may be amplified to allow detection of the hybridization. The detectable parameter may be any measurable quantity that indicates the presence or absence of the hybridized materials. Under illustrated embodiments the optical or conductive properties of the hybridized materials may be amplified 412 for purposes of detection. Amplification, in this case occurs by plating a silver solution onto the nanoparticles of the hybrid.

Amplification may occur by passing a silver A solution and a silver B solution through the hybridization chamber 140, 142, 144, 146. To pass the silver A solution and silver B solutions through the hybridization chamber, the controller 300 may execute a set of instructions 380 that causes silver A valve 320 and the silver B valve 316 to form a connection between ports 1 and 3. The silver A pump 306 and silver B pump 302 may then be activated by the instructions 380 to draw the silver A solution from the silver A container 332 into the silver A pump 306 and the silver B solution from the silver B container 328 into the silver B pump 302.

The silver A valve 320 and the silver B valve 316 may then be instructed to form a connection between ports 2 and 4. The waste valve 326 may be instructed to form a connection between ports 2 and 4. The instructions 380 may specify a discharge rate for silver A pump 306 and the silver B pump 302 and the controller 300 may activate the pumps 306, 302 to discharge at those rates. The silver A pump 306 may discharge into port A and the silver B pump 302 may discharge into port B. The instructions 380 may also specify a intake rate for the waste pump 312 equal to an output of the silver A pump 306 and silver B pump 302 and the controller 300 may activate the waste pump 312 to withdraw fluid from the port C at the selected rate. Once the silver A pump 306 and the silver B pump 302 have discharged their materials into the respective ports and the waste pump 312 has been filled with fluid withdrawn from port C, the valves 316, 320, 326 may again be moved under control of the instructions 380. The silver A valve 320 and the silver B valve 316 may be positioned to again fill the silver A pump 306 and silver B pump 302 with silver solutions. The waste valve 326 may be positioned to discharge withdrawn materials into the waste container 338. The fill and empty steps may be repeated by the number of cycles necessary for sufficient amplification of the hybridized materials again under the control of a counter and comparator based upon a cycle limit value.

Figure 13:
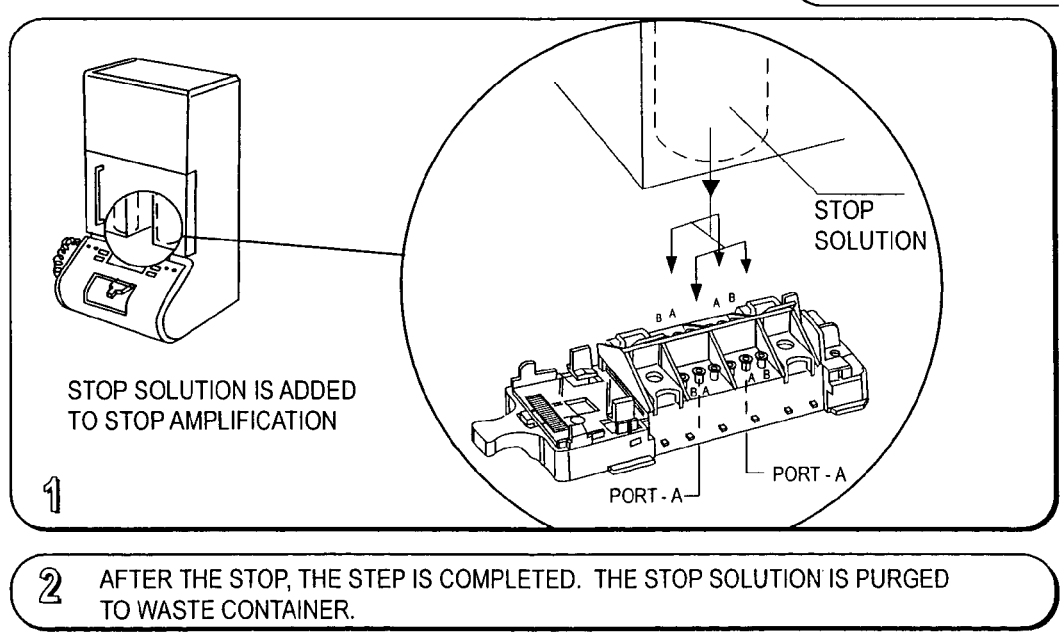
FIG. 13 depicts an amplification stop step that may be used with the sample processing system of FIG. 1.

Once the amplification step has been completed, a stop solution may be passed through the hybridization chambers 140, 142, 144, 146 as shown in FIG. 13 to stop amplification 414. In this regard, a set of stop instruction may be executed by the controller 300 to position the stop valve 318 with a connection between ports 1 and 3. The stop pump 304 may be activated to fill the pump 304 from the stop solution container 330. The controller 300 under control of the instructions 382 may then move the stop valve to form a connection between ports 2 and 4 and the waste valve to form a connection between ports 1 and 3. The controller 300 may then select a discharge rate for the stop pump 304 and activate the stop pump 304. The controller 300 may select the same withdrawal rate for the waste pump 312 and simultaneously activate the waste pump 312 to pull the stop solution through the hybridization chamber 140, 142, 144, 146. The valves 318, 326 may be repositioned to refill the stop pump 304 and empty the waste pump 312 and the process may be repeated.

Under an even more preferred embodiment, the pumps would never be refilled. In this case, the pump bodies are integrated into a reagent cartridge that is simply replaced when empty.

Figure 14:
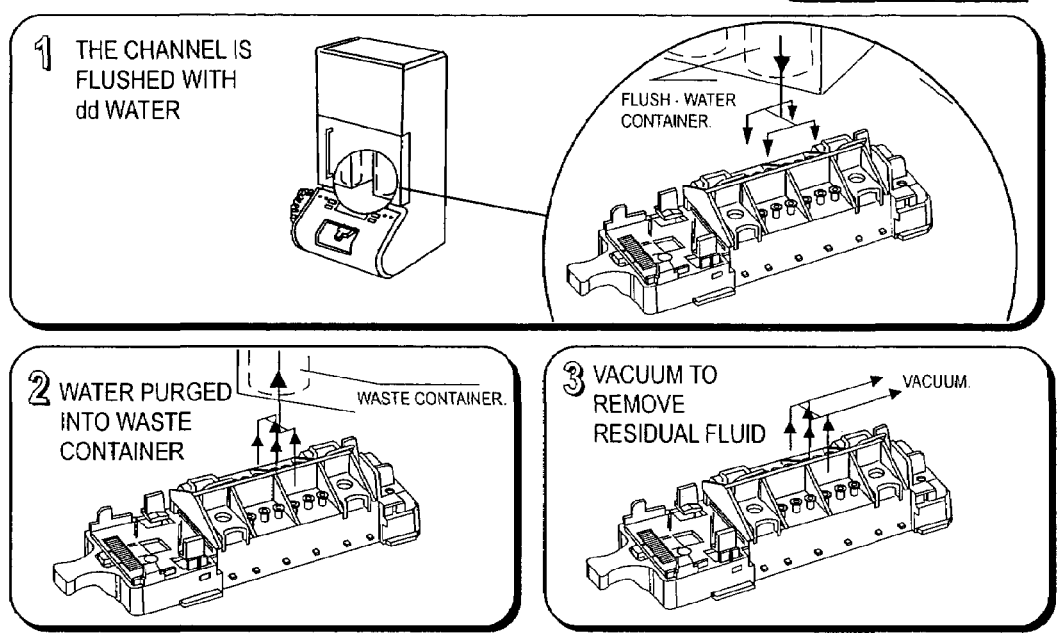
FIG. 14 depicts a flushing step that may be used with the sample processing system of FIG. 1.

Once the stop solution has been passed through the hybridization chamber 140, 142, 144, 146, the hybridization chamber 140, 142, 144, 146 may be flushed 416 with dd water and vacuumed to remove residual fluid as shown in FIG. 14.

To flush the hybridization chambers 140, 142, 144, 146, the controller 300 operating under flush instructions 384 may move the flush valve 322 to form a connection between ports 1 and 3 and activate the flush pump 308 to fill with water from the water container 334. The controller 300 may then reposition the flush valve 322 to allow the flush pump 308 to discharge into port A and reposition the waste valve 326 to withdraw fluid from port C. Once the flush pump 308 is empty, the valves 322, 326 may be repositioned to refill the flush pump 308 and empty the waste pump 312 and the process may be repeated.

Once flushing is complete, the controller 300 operating under control of instructions 384 may activate the vacuum 314. The vacuum 314 may pull any remaining fluids out of the hybridization unit 20 by displacing the fluids with air pulled in through the respective sample wells 108, 110, 112, 114.

Figure 15:
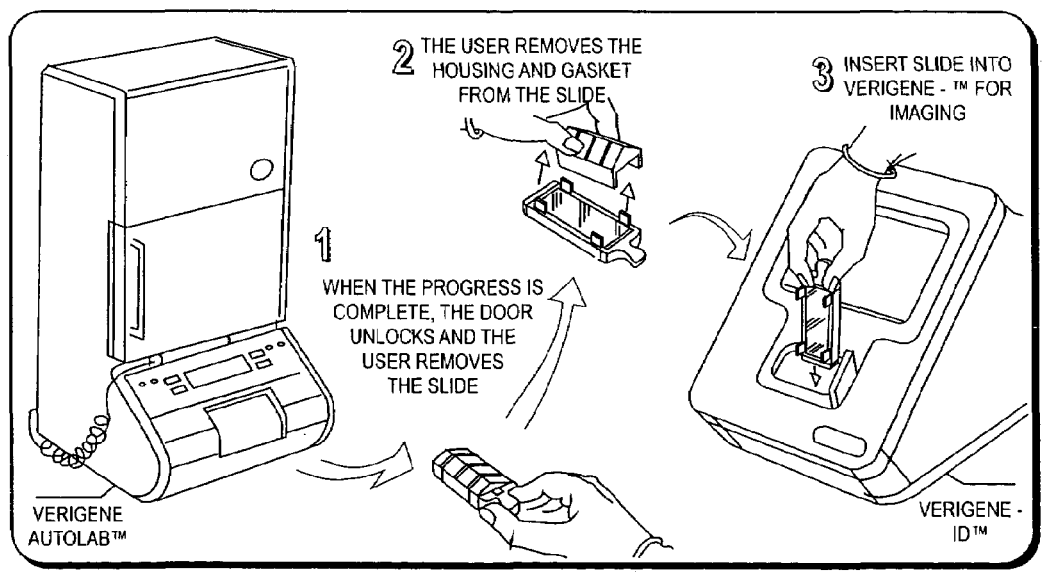
FIG. 15 depicts disassembly of the hybridization unit and reading of the substrate within the optical reader of FIG. 1.

Once any remaining fluids have been removed, the sample processing unit 12 may unlock as shown in FIG. 15 and the hybridization units 20 may be removed. The substrate 58 may be removed from the hybridization unit 20 and placed in the optical reader 14 where the optical characteristics of the hybridized sample may be read.

Figure 2:
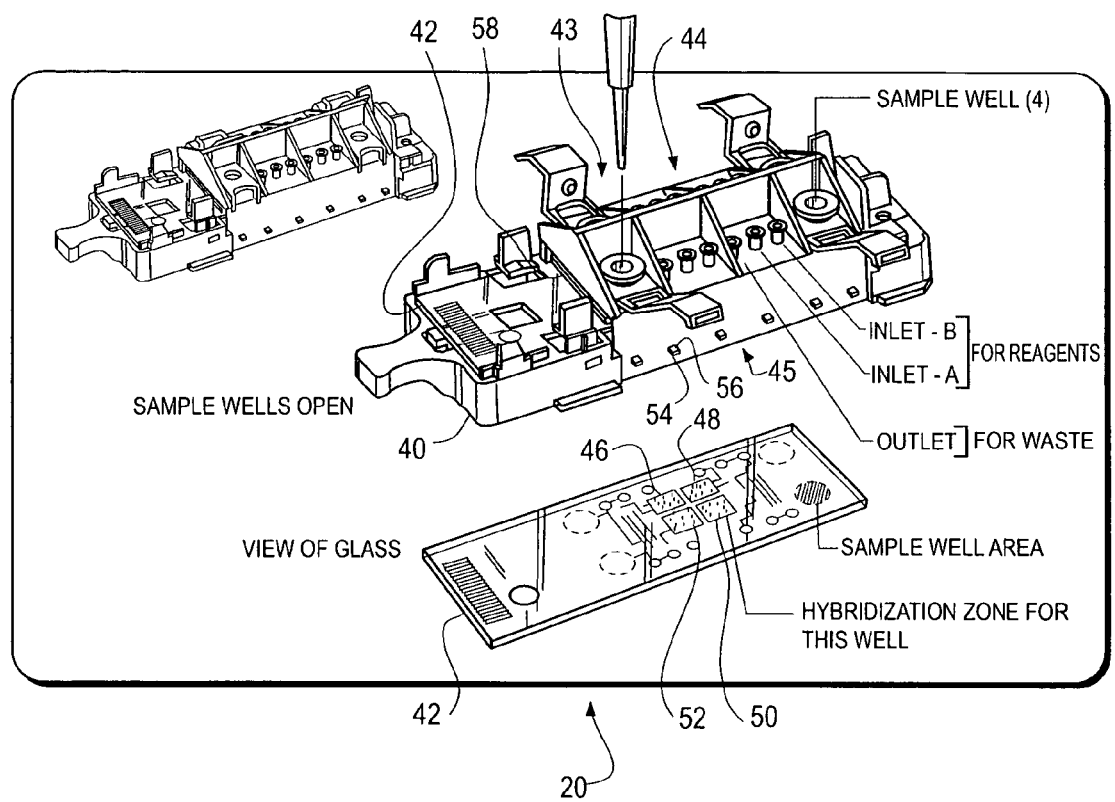
FIG. 2 depicts a hybridization unit that may be used with the system of FIG. 1.
Figure 18:
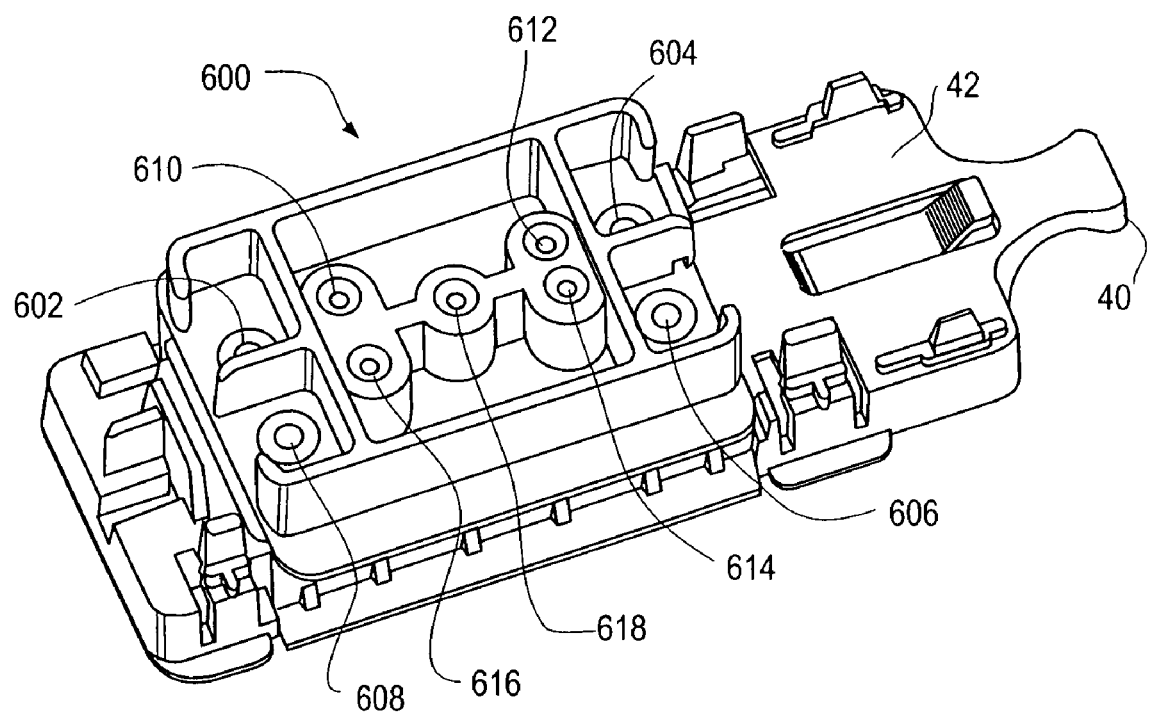
FIG. 18 depicts a distribution manifold that may be used with the system of FIG. 1 under an alternative embodiment of the invention.
Figure 19:
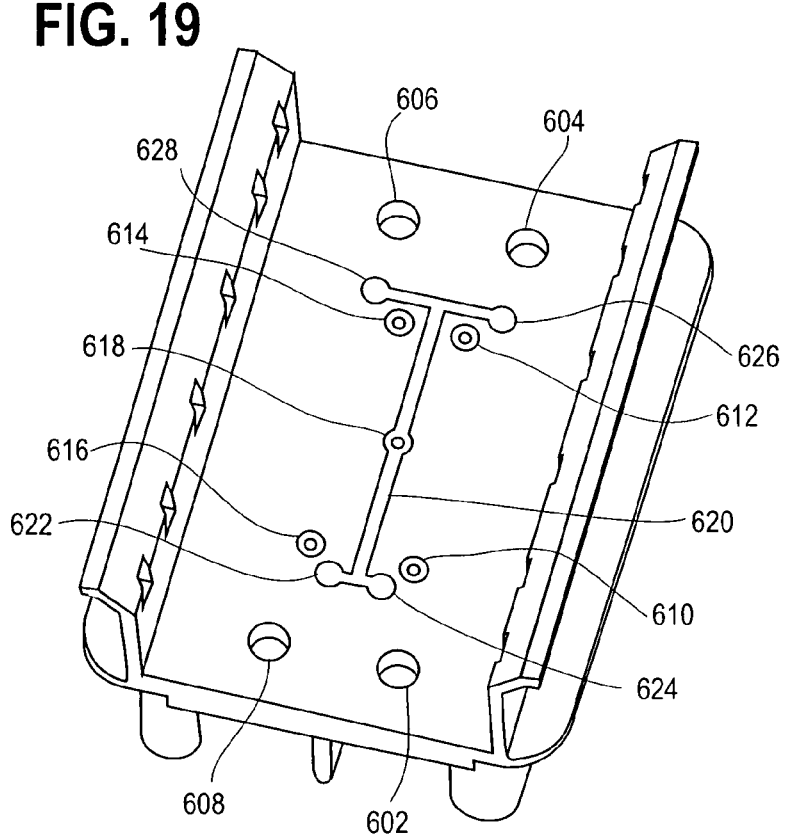
FIG. 19 depicts an underside of the distribution manifold of FIG. 18.
Figure 20:
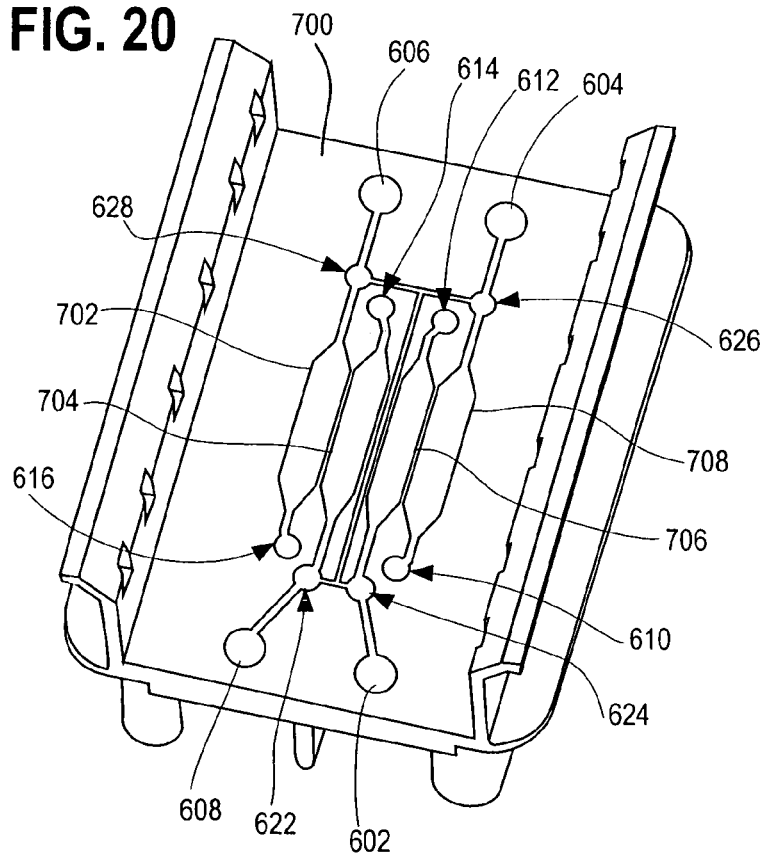
FIG. 20 depicts a gasket that may be used with the distribution manifold of FIG. 18.

In another illustrated embodiment of the invention (shown in FIGS. 18-20), the distribution manifold 44 shown on the hybridization unit 20 of FIG. 2 is replaced with a distribution 600 (shown as a complete hybridization unit 20 in FIG. 18). FIG. 19 shows a reverse view of the manifold 600. FIG. 20 shows a gasket 700 that may be used with the manifold 600 of FIGS. 18 and 19.

As with the manifold 44 of FIG. 2, the distribution manifold 600 of FIG. 18 has sample wells 602, 604, 606, 608 in opposing corners. This distribution manifold 600 has four waste ports 610, 612, 614, 616 associated with a respective hybridization zone 708, 706, 704, 702 (FIG. 20). Also shown in FIG. 19 is a common fill port. The manifold 600 of FIGS. 18, 19 and 20 is believed to be particularly well adapted for use with the system of FIG. 21.

FIG. 19 shows an underside of the distribution manifold 600 of FIG. 19. As shown, each of the ports 602, 604, 606, 608, 610, 612, 614, 616, 618 of FIG. 18 has a corresponding feedthrough 602, 604, 606, 608, 610, 612, 614, 616, 618. It should also be noted that the fill port 618 has a channel 620 disposed on a surface of the distribution manifold 600 that terminates at four feedthrough points 622, 624, 626, 628.

Turning now to the gasket 700, it may be noted that the gasket 700 defines the hybridization chambers 702, 704, 706, 708 and a number of connecting channels. For example, the first hybridization chamber 702 has a connecting channel that connects the sample well 606, feedthrough 628 and the first end of the hybridization chamber 702. The first hybridization chamber 702 also a connecting channel that connects a second end of the hybridization chamber 702 to waste port 616.

The second hybridization chamber 704 has a connecting channel that connects the sample well 608, feedthrough 622 and the first end of the hybridization chamber 704. The second hybridization chamber 704 also a connecting channel that connects a second end of the hybridization chamber 704 to process port 614.

The third hybridization chamber 706 has a connecting channel that connects the sample well 602, feedthrough 624 and the first end of the hybridization chamber 706. The third hybridization chamber 706 also a connecting channel that connects a second end of the hybridization chamber 706 to process port 612.

Similarly, the fourth hybridization chamber 708 has a connecting channel that connects the sample well 604, feedthrough 626 and the first end of the hybridization chamber 708. The second hybridization chamber 708 also a connecting channel that connects a second end of the hybridization chamber 708 to process port 610.

It should be noted that the fluid manifold 72 and pump connections with the processing unit 12 may also be changed to accommodate the distribution manifold 600. It may be noted in this regard that port connections A and B in FIG. 5 would be combined and connected to the respective process port 610, 612, 614, 616. The waste port 618 in FIG. 18 would correspond to port C in FIG. 5. In other regards, a hybridization unit 20 using the distribution manifold 600 would operate substantially the same as described above.

In another illustrated embodiment of the invention, the manifold 72 may be provided with a connection to replaceable cartridges for the hybridization buffer and/or probes. Under this embodiment, the user would simply add the target sample to the test wells and insert the hybridization unit 20 into the sample processing system 12. The system 12 would add any missing elements to the sample wells.

A specific embodiment of method and apparatus for processing nucleic acid samples has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention and any and all modifications, variations, or equivalents that fall within the true spirit and scope of the basic underlying principles disclosed and claimed herein.

The invention claimed is:

1. An apparatus for preparing a test sample for purposes of detecting a predetermined target nucleic acid, such apparatus comprising:
a test probe comprising a oligonucleotide attached to a nanoparticle;
a hybridization unit containing the test sample and the test probe, wherein said hybridization unit further comprises a target sample substrate, a distribution manifold coupled to a first side of the substrate and a hybridization chamber, the distribution manifold having a plurality of passageways;
a processing fluids manifold having a plurality of passageways clamped to the distribution manifold of the hybridization unit;
a gasket disposed between the substrate and the distribution manifold that defines the hybridization chamber between the gasket and substrate and that also defines a plurality of passageways extending parallel to and between opposing surfaces of the substrate and distribution manifold where each passageway of the gasket interconnects the hybridization chamber and a respective passageway of the processing fluids manifold through a respective passageway of the distribution manifold;
means for denaturing the test sample; and
means for preparing the test sample for detecting the predetermined nucleic acid by pumping a plurality of processing fluids between the processing fluids source manifold and distribution manifold where each processing fluid of the plurality of processing fluids is pumped through a respective passageway of the processing fluids manifold, the distribution manifold and gasket to hybridize the test probe and predetermined target nucleic acid to the target sample substrate, to wash the hybridized sample and to amplify a detectable parameter of the nanoparticle of the hybridized sample.

2. The apparatus for preparing the test sample as in claim 1 further comprising a hybridization solution disposed in a sample well disposed in the distribution manifold of the hybridization unit.

3. The apparatus for preparing the test sample as in claim 2 further comprising the test probe disposed a sample well disposed in the distribution manifold.

4. The apparatus for preparing the test sample as in claim 1 further comprising the test sample disposed in a sample well of the hybridization unit.

5. The apparatus for preparing the test sample as in claim 4 wherein the means for denaturing the test sample further comprises a heater adapted to heat the sample well.

6. The apparatus for preparing the test sample as in claim 5 further comprising an oligonucleotide having a sequence complementary to a first portion of a genetic sequence of the predetermined target nucleic acid disposed within a hybridization zone of the hybridization unit.

7. The apparatus for preparing the test sample as in claim 6 wherein the oligonucleotide disposed within a hybridization zone of the hybridization unit further comprises the oligonucleotide physically connected to the target sample substrate.

8. The apparatus for preparing the test sample as in claim 7 further comprising defining the oligonucleotide attached to the nanparticle as having a genetic sequence complementary to a second portion of the genetic sequence of the predetermined nucleic acid.

9. The apparatus for preparing the test sample as in claim 8 further comprising a first pump adapted to draw a content of the sample well from the sample well into the hybridization zone using a fluid coupled through a first port of the processing fluids manifold.

10. The apparatus for preparing the test sample as in claim 9 further comprising a cooling element adapted to chill the content of the sample well as the content is drawn into the hybridization zone.

11. The apparatus for preparing the test sample as in claim 9 further comprising a second pump adapted to hybridize the probe and predetermined nucleic acid with the oligonucleotide connected to the target sample substrate by shuttling the content of the well through the hybridization zone a predetermined number of times.

12. The apparatus for preparing the test sample as in claim 11 further comprising a third pump adapted to flush the hybridized probe, predetermined nucleic acid and oligonucleotide connected to the target sample substrate by introducing wash fluid through a second port and discharging wash fluid through the first port.

13. The apparatus for preparing the test sample as in claim 12 further comprising a fourth and fifth pump adapted to introduce and mix fluids to amplify optical characteristics of the hybridized probe, predetermined nucleic acid and oligonucleotide connected to the target sample substrate by introducing a plating solution through a second port and discharging spent plating solution through the first port.

14. The apparatus for preparing the test sample as in claim 13 further comprising defining the plating solution as being a silver solution.

* * * * *